US012565662B2

(12) United States Patent
Lai et al.

(10) Patent No.: US 12,565,662 B2
(45) Date of Patent: Mar. 3, 2026

(54) PLANT PATHOGEN EFFECTOR AND DISEASE RESISTANCE GENE IDENTIFICATION, COMPOSITIONS, AND METHODS OF USE

(71) Applicant: HUAZHONG AGRICULTURAL UNIVERSITY, Hubei (CN)

(72) Inventors: Zhibing Lai, Hubei (CN); Bao Zhang, Hubei (CN); Jiali Wang, Hubei (CN); Junshi Huang, Hubei (CN); Hongze Wang, Hubei (CN); Haoxuan Min, Hubei (CN)

(73) Assignee: HUAZHONG AGRICULTURAL UNIVERSITY, Wuhan (CN)

( * ) Notice: Subject to any disclaimer, the term of this patent is extended or adjusted under 35 U.S.C. 154(b) by 86 days.

(21) Appl. No.: 18/555,464

(22) PCT Filed: Mar. 31, 2022

(86) PCT No.: PCT/CN2022/084239
§ 371 (c)(1),
(2) Date: Oct. 13, 2023

(87) PCT Pub. No.: WO2022/218158
PCT Pub. Date: Oct. 20, 2022

(65) Prior Publication Data
US 2024/0191249 A1      Jun. 13, 2024

(30) Foreign Application Priority Data

Apr. 16, 2021    (CN) .......................... 202110403600.2

(51) Int. Cl.
*C07K 14/415*      (2006.01)
*C12N 15/82*      (2006.01)
*C12Q 1/66*      (2006.01)
*C12Q 1/6895*      (2018.01)

(52) U.S. Cl.
CPC ........ *C12N 15/8279* (2013.01); *C07K 14/415* (2013.01); *C12Q 1/66* (2013.01); *C12Q 1/6895* (2013.01); *C12Q 2600/13* (2013.01); *G01N 2333/90241* (2013.01)

(58) Field of Classification Search
CPC ............ C12N 15/8279; C12N 15/8282; C07K 14/415; C07K 14/375; C12Q 1/66; C12Q 1/6895; C12Q 2600/13
See application file for complete search history.

(56) References Cited

FOREIGN PATENT DOCUMENTS

WO      WO2019/236257      12/2019
WO      WO-2021211227 A1 *  10/2021    ........... C07K 14/375

OTHER PUBLICATIONS

Deng et al., The RppC-AvrRppC NLR-effector interaction mediates the resistance to southern corn rust in maize.2022. Mol. Plant 15, 904-912 (Year: 2022).*
Chen, G. et al., Cloning southern corn rust resistant gene RppK and its cognate gene AvrRppK from Puccinia polysora. 2022 Nat Commun 13, 4392 (Year: 2022).*
Cantu et al., Genome analyses of the wheat yellow (stripe) rust pathogen *Puccinia striiformis* f. sp. *tritici* reveal polymorphic and haustorial expressed secreted proteins as candidate effectors. 2013. BMC Genomics 14:270 (Year: 2013).*
PCT Search Report and Written Opinion prepared for PCT Application No. PCT/CN2022/084239, completed Jul. 6, 2022.
Yoshida, Kentaro, et al., "Association Genetics Reveals Three Novel Avirulence Genes from the Rice Blast Fungal Pathogen *Magnaporthe oryzae*", 2009, The Plant Cell, vol. 21, No. 5, pp. 1573-1591.
Fang, Anfei, et al., "Identification and Characterization of Plant CellDeath-Inducing Secreted Proteins From Ustilaginoidea virens", 2016, Molecular Plant-Microbe Interactions, vol. 29, No. 5, pp. 405-416.
Lorrain, Cecile, et al., "Advances in understanding Obligate Biotrophy in Rustfungi", 2019, New Phytologist, vol. 222, No. 3, pp. 1190-1206.
Saur, Isabel M., et al., "Conclusions", 2019, Plant Methods, vol. 15, No. 1, p. 118.
Austein, G. McLoughlin, et al., "Identification and application of exogenous dsRNA confers plant protection against Sclerotinia sclerotiorum and Botrytis cinerea", 2018, Scientific Reports, vol. 8, No. 1, pp. 2, 5, and 6.
Salcedo, Andres, et al., "Variation in the AvrSr35 Gene Determines Sr35 Resistance Against Wheat Stem Rust Race Ug99", 2017, Science, vol. 358 No. 6370, pp. 1604-1606.

* cited by examiner

*Primary Examiner* — Amjad Abraham
*Assistant Examiner* — Christian Jose Ordaz
(74) *Attorney, Agent, or Firm* — Barnes & Thornburg LLP

(57)      ABSTRACT

The compositions and methods are related to plant breeding and methods of identifying and selecting disease resistance genes and plant pathogen effector genes. Provided are methods to identify novel genes that encode plant pathogen effector proteins and proteins providing plant resistance to various diseases and uses thereof. These disease resistant genes are useful in the production of resistant plants through breeding, transgenic modification, or genome editing.

11 Claims, 3 Drawing Sheets

Specification includes a Sequence Listing.

SEQUENCE LISTING

```
<160> NUMBER OF SEQ ID NOS: 5

<210> SEQ ID NO 1
<211> LENGTH: 8232
<212> TYPE: DNA
<213> ORGANISM: Puccinia polysora

<400> SEQUENCE: 1
gatgagatgt gtgtgatgtg atggagatgg gactggtatg gatttgctga tgtggatggg      60
tgttttagat gtgatggatg gtggatggat gatgatgaat aaatggctgg tttgatgttt     120
gaaatctgcc attttcatga aacccgctat tttgaaatac accagttagg gggtatgtgt     180
atttcagaaa tccgccatta aaaatggcag tttttgtcaa aaaaatgtca ggtttctaat     240
ggcgggtttg ctaactctga aacgccctaa tatagaaaaa ataattatta aaataatgct     300
ttttggtata cattcccact gcaggaaggt attcaaaatt tgaaaatcca tgccaataaa     360
aaaaggtatg aatgtagaac ttgaaggttt gaaaaaactt ttcaaggttt aaagaaatgc     420
ctggggtggg aaaacaagcc tcttgagggt gtttacaggc ctgtcaagtt taaaaggacc     480
tcctgggtta gggaaacaag tattttaaag ctctacagat cacttgggtt gtgaaaaaac     540
accttttgag aaggcattga gcctatgaat gcatttaaat atgaatgtgg gccttggggg     600
gctaaaataa gcccccaaat cccctgtggg gtcttcctgg ggaagggtct ttttgagaat     660
tcaattattg aaatcacttg agttaattca acatgtaaag ataagacaaa tttcaagttt     720
gaaagaaata acaacctgag ctcagatttg acaaatcaac accttgggtt gtgtgtttta     780
gttttttgtt gtaaaacaca tcaaaataca tgttattagt aattaacagg ggatgaattt     840
acccttttca agctttagtc ttttgatcaa atactaatcc tcatgtatct attccattta     900
gagcttgaga tttcatactg gaatcaaaaa gttggcaatt ttttaattaa ttcaaagttt     960
ctacttgaca atttctgaat atctattcca ctcaaagtta ccagttaccc aaatttgaat    1020 ttattttaa  taggccctca  aaaattcaaa  ttttcaacat  ttatatttcc  tgtttttcat  1080
ttgattcttg aattaaaggg gaataaaattc atcatttttg aaaacatcaa tatttctgtg    1140
```

-continued

```
acctttttga aaattgaaaa attggtgaag attagggctc aggatcaagt attctatata    1200
tttcctagat taatgggcaa tttgcaattt gaattcagaa gaaatggttt caggtattat    1260
ttttgacttt gatatggcct aatccttggt ctaaactgaa aaaaattctt ttagatttcc    1320
aacataaata ttttttcttc tttgaatatt tactaggaaa tatgatgact acaatgagac    1380
ttgatcactt ttaatcaacc aattttcaca ttgaatttat acttctacta aagagtacct    1440
tctgttttta ataatataaa ttctttataa taattatccc ttcaaaaaaa aagaattttc    1500
atgcataatt caccatctaa atagttcatt tgaacaagct tggacacctt gtggcaaaga    1560
aatcaccaaa aaaacaggtg aaatgactga cctttgaaag gaaaacatga tgtatttta    1620 aattatatat aagtttggaa cttcaggtaa aatagggccc aagaatctat ttgaatttca    1680
taaggtaatt ttttttttgaa ttttgatttg atttaaaact gacatatatg aataaattca    1740
agaagattga actgagtatg atcagaacca ttaatcaatt gtcaaaattt gctaaattgt    1800
gcaggggaac cagataataa aaaaaaataa ctgataaatt gtgctatctt tcatcaaatt    1860
aataatgttt ttgcctttg tgatacagat aaaaattata cagaaatttc atcacaaaca    1920
ttcaatgcag atgaaaacat gcaaagtttt tcttttggtt tcctcaataa atattacctg    1980
catttcactt tggaaaactc attggattaa atctccttag tgagttaaat ccatcatctg    2040
atcttccgat ttatctacta taaattgatt ttttttttca aatagaattg aattcatcag    2100
ttgatatcac cagaaggacc ccctctgaga cttgtaggca gctcatacct aaaaattgaa    2160
ccaatttgac aacccaggat ggaagaagtt gccaataatc agtccaaaaa tatcaagaat    2220
tcactcaaat attatcaatt aattccaata aagatacatc aatttttcat caattaccaa    2280
aaaattatat aaaaactta tgatttggtc ccttgtctct attcttgaga aagatgagtg    2340
atctttagtc tgtctttgtt ccaggttatt tcactgtgga tattctgagg caggcactgt    2400 gcttactcc tacaacaatt cttacttaga ataaaaaaat taatgataaa aattgaaatt    2460
tccaactaaa aatttgattc accaatgatc ttgtctgatt attaaatatc tactcaactt    2520
cagagtagga aaatgattaa aacctttttt gtaattttt catagaaaaa aaaggggtca    2580
tctaaatgac tttagacctc ataaaatcca agacagttca ataaattctg aaaaatgtcc    2640
aaaataactt aactttcctt tttttattaa cagcaaaata aattgagact gttttataga    2700
aaatatgtgg gataccagga aatgagattg tggattgaat aacaaggaa gctataaaaa    2760 atgcatccaa accacctatt ccccaccaga gatgactagg aaaaaaagat gcaggattgg    2820
ctctaggcta acatgagcca aaaaagaata acccaaacct tgattagaat atggctatgt    2880
ggtctggttg attaaaactc tctcaaatga attctcaaga actgaatatt tgtttagaaa    2940
aaaaaataaa taaattcact aaccctctcc gcccctacc cccattttt tggaagaaaa    3000 ttgaacagtt taaaaattta ctcgattgtt ttcctggccg aaggaaatta aagaagcact    3060
cggaggaacc atctaaggca caatcaaatc taatataatt ttaaacctct aaattttttt    3120
ttaaaaatca cttgaacaaa atttcaactc actaaaacaa gatcttaaac aatccaaagc    3180
caatccttcc cgggctgaaa caatcgaatc caatacaatt atcaagcctg ctgggtttg    3240 aattgcctag gatgatcaaa atctccctga tccagcgtcc aacgtacaat cctttgaacc    3300
catctgagac ccaattcctg tccacccact atttgatttt gctctttcta agtattgtgg    3360
tatctgtgtt gatgattatt atctttcctt ttttttcgccc gcttactttc taattttcct    3420
tttgatcttt catcttttcg ctctttcctt tcggctttgg gttttttgatc tctgttattt    3480
```

-continued

```
tcctttcccc cccccctct ttcgcctttc ttgcctccgc tcgatcctct ttctccacat    3540
atcatctcac tttcttgatt ccttccgatc ctccttaatc agaagcccta gaccccccgg    3600
tgtttagacc ctcgcactag cccggggtga agaaggtgac tcacgaaacc ccgactacgg    3660
ggtaaaccat gttttttacga gtttcatagc gtgcaatacc gtagccgaca tcatacctga    3720
aacgacaaaa aaggaaatgg atggagaggt cgagtttgaa gcaaagcatg atgagtggaa    3780
tcgggtcaac tgaaacctga tctcatgcta agattctcta gagttcggac gatatatcct    3840
catcattcgt tcggggttct tttattttc attttaattt cttccgtctt gtggtgcagc    3900
tagtcatagc tagctaatga tgctactcga tcgatgattt tttctggttg ttgatggttg    3960
ttgagtagtt ttaccggact ggacccatca gcaggtttca tcgtctgttc cgtccatccc    4020
agatgtcgca ataagagtag tgatgatatt cctaaattaa atattcactc aatcgacctt    4080
attacatacc cccacccaaa accggcgatt gggatagtgg agcgactcga ccatctggcc    4140
ggctggctgt gatcctggtt ggttggtgcc gcacaaatat gtaaatcgta tgtaagtgca    4200
tacaatcccc attagcatgt ttgtttctca tggtggagtg tccgcaacgc cgtctgactc    4260
tgatgcccat tgccattcac tcctggatac caccttggca cctacccact tgagtacgta    4320
ttcaggtttg gacccaccca atcacttacc tggattatct cagtctccac tctgcagtat    4380
gaatgtcaat gggagccctg tagacattca aatgaaaaat gtgcattctg ttgaatccaa    4440
gcctgtagtt atgatctctt ctgcccgcag tgctctgtag tgtctcaata cacctgatcc    4500
gtttttggag ctgtacgcac acatctttgc ttacctatac gtatacacag gtatgaggtt    4560
atgtatttgt gtatgtatgt gcatacatgg tcagtgccta gtcctacggt atctatgtaa    4620
atatgcctgc acgcatgtgt tgacatcctc gtccactggg gtcgtaaagt atgtacatat    4680
ttatgcataa attctcgcag acggggagag agggactagt gagactaacg agggagaggg    4740
aaacccccta cccagagggc gagcgcgacc agccctgggg gggcccaatc ggaagctgaa    4800
agccaagttc ccattgcctc accattctag cccggctctt gacccctga gtccctcttc     4860 agccgataag aaactgagaa agaaaaattg ataaaaagtc catcgaagga tcgattcatc    4920
cgtcgaattc aactcgagac caacctagaa acccgtcatc acccaccaag tcaaccgcaa    4980
gctccaagtc aggtaatctc ctcaagatga aggagagttc gagtaatacg gactttgatg    5040
atatttacgg tcccaacgac gatgccccag aagtacatcc gcattcctga ttctctatcg    5100
ttgtcttctc gcttctcttc tcttctctcg ctctgtctcg ctctttctct ctctctctct    5160
ctctctctct ctctctcgct ctctctctct ctctctggct ctctctccat ctttctctct    5220
ctcgcgtcga tggtcatcat cccccatcca tctggtcttg gttcttgtct tgctctcgtc    5280
ccgtcctctc catcgatgtc tccctcgccc tttgtctctc cgtcttctcc aaccatcgac    5340
gtataccacc cagtcgacgg tctatttcct cccagagatt accttccatc tcttgccttg    5400
ttctctccat cccaatccct ggtcatcgtc ttcgattgtc agacctccag ccgctgcttg    5460
tttccctctc tcccccggtt ttcgttttac tcgaccgatt tgtccatgtc ccatccgcct    5520
ccgtctccct ccaatctccc ccattcccct cctcccctct ccaccctcat cgcccctcct    5580
aagcttgatt catcggatgc ctcccctgtc gctcgctcga aatcgatcgt cattacgacc    5640
gagtctttct tcccatctca tggcccgatt taactcttgt cctccaaccg attgtgggcc    5700
caacacatgg cacgataacc acgaactggg actccctccc ctgtgatcct tcctcttact    5760
cattccacgt cacccattat atcccctca tccctccaca acgttgtaga tatacttgtg    5820
aaatacggtt gatgataccg actgattgtg gatcagtctc ggggcgttgt ctgtctcttc    5880
```

```
tcctgctacg cacttgtctg cgaccttgta tcatccgcct cgatccattc cctacccagc    5940 ttgtttttgat cccgtctccc tcagcatctt cgaactcgtc ctctcctgta ataacctctt    6000
cacctccaac cttttcaccc tttgcatctc tccctctctc ttgcttctta ctcgacgtat    6060
ccgctgaccc aacgagtcaa gggcctgatg ggcaagaagt tattcatcct gcttcttcca    6120
ttctcacttg tatctgtttt cacgtctgac gcatccaccg ggcttgtttt ttactctctc    6180
gtctcgcttc tcccgaggcc gtatgtaaac ttgttggaaa accaccgaac cacatctgca    6240
ctgatcgttt ttttttgttg tcgatgtctc atccaaccct ctcactgcaa cctcaggagc    6300
gctcatgtgt atcatctccc ttcttaactt tgggttccaa tcactccgaa aactgccttg    6360
tgtttgaagt ccaactcaac tgtttgccat ctgaacctgt cattcatcaa ccgccaacct    6420
gagaaaacaa accgatcttg ttgtttccac ttgaaaacca tgtgttcttg aacctccact    6480
cggacttatt gatgtggtta atgactaaag aaccaatgtg atgggcatgc tgcgtttagg    6540
agagaaccaa taacaaagcc agttatccat tgatctattg atccgttgcc tcattgaaca    6600
cattgtgcga cgaacatcga tccatctgga aatgaaaccc gaacgaaata tcacattcgt    6660
tttgcagcgg aaactttttcc atcacctctc gtcctgattt cgctttgacg cctgtatgaa    6720
gttgtttctc tcgggactga tcttacgaga gtggggtttt tcctagagtg gagcagggcc    6780
tatcggcgcc tcgaattgat cccagtctat ccaagcgata ttcggttccc aaatcatgac    6840
gcgaaatgtt acgttgggtt gtgacgctat gagggggcag ggtgtcttac gattgttttg    6900
ttattccatc tcccatcgat acgttctcta ggataatttg tatgcagacc tgataccaga    6960
ggatggttcg actactgtca gcaaccgaga tcccaccagc ccgactcggt acgatgcggt    7020
tcttaggaaa tcgtcgacga accacgattc acccctcaaa ggtaatactg atgagaatcc    7080
tacctcgacc acgacgacga ccacacccac caccaagcct catcatactc atccaggtgg    7140
tgagtcgagc aacgcatcgg acatcaaacc ggatatcaaa cctggtggtc accatgaggt    7200
agagagagat ttcctgcttc atcttacctt tccaaagcga aaaaaaaaa aatccatcaa    7260 caaaacttag ggcccagtcc agcccctatc atgacatact agtacatcaa tagatactct    7320
tatgataaaa tcaaagtgtt tgaacgacta gttgcgtagg gaacttgggt cacgttttaa    7380
ccatgacgac tttcccttcg tccgctcgat ataacttttg atgttgcctt cgttcaatca    7440
tcatcatcgc aatgagttag aactgactca acatcatcct atccaacgtc tgcctttatc    7500
atctgttctt ttactctatt tctcatcaat atccatccac ttcatcaccg cgttgcacaa    7560
ccctacgcgc gatgggccac aaatcaatcg atagcatggg ttaccgatcc cacccatgtc    7620
ggcctcatta ccagcaaacc cgatggcgac caattcaaag cagggtggga cgagtggacc    7680
tggaggctca ttagctacgt cgtcgatacc gacgagtagt accaataact ctggcttggg    7740
tggtgccagt agtagtgctc cttcccatca gcaacaccaa ccaatcggta ccctcacccc    7800
acccacgacc cacaaacaca accatcatca gcttcacaat aataatagca gcaacagtca    7860
ccactccaat catgatcaga tgatgaacaa tagtaccaac aatcctatca gctcccatca    7920
cccctctcat cataaccagt actccaatct ccacacgttc aactcaaccg ccctgggggc    7980
cagaaaggat gagcgtggct tatgcggact ctatatcgct gatttacaat gggttagtag    8040
tgtataccga gctgctccta atccttcacg actgatccca tagaacctcc agggactgac    8100 ggccccttcat tttacgggtc tgcgcgggcg cgggtcttcc ttctttcccc ttcggtgggt    8160
tcccttctct tgaccccgtgg gtgctttacg tagtacacga gtgatgaaga tctacgtaag    8220
```

```
gtcgccgaga ac                                                             8232
```

<210> SEQ ID NO 2
<211> LENGTH: 733
<212> TYPE: DNA
<213> ORGANISM: Puccinia polysora

<400> SEQUENCE: 2

```
ccctctctcc cccggtttttc gttttactcg accgatttgt ccatgtccca tccgcctccg       60
tctcccttcc aatctccccc attccctcc tcccctctcc accctcatcg ccctcctaa         120 gcttgattca tcggatgcct ccctgtcgc tcgctcgaaa tcgatcgtca ttacgaccga        180
gtctttcttc ccatctcatg gcccgattta actcttgtcc tccaaccgat tgtgggccca       240
acacatggca cgataaccac gaactgggac tccctcccct gtgatccttc ctcttactca       300
ttccacgtca cccattatat cccctcatc cctccacaac gttgtagata tacttgtgaa        360
atacggttga tgataccgac tgattgtgga tcagtctcgg ggcgttgtct gtctcttctc       420
ctgctacgca cttgtctgcg accttgtatc atccgcctcg atccattccc tacccagctt       480
gttttgatcc cgtctccctc agcatcttcg aactcgtcct ctcctgtaat aacctcttca       540
cctccaacct tttcacccttt tgcatctctc cctctctctt gcttcttact cgacgtatcc      600
gctgacccaa cgagtcaagg gcctgatggg caagaagtta ttcatcctgc ttcttccatt       660
ctcacttgta tctgttttca cgtctgacgc atccaccggg cttgtttttt actctctcgt       720
ctcgcttctc ccg                                                           733
```

<210> SEQ ID NO 3
<211> LENGTH: 318
<212> TYPE: DNA
<213> ORGANISM: Puccinia polysora

<400> SEQUENCE: 3

```
atgataccga ctgattgtgg atcagtctcg gggcgttgtc tgtctcttct cctgctacgc        60
acttgtctgc gaccttgtat catccgcctc gatccattcc ctacccagct tgttttgatc       120
ccgtctccct cagcatcttc gaactcgtcc tctcctgtaa taacctcttc acctccaacc       180 ttttcacccct ttgcatctct ccctctctct tgcttcttac tcgacgtatc cgctgaccca      240
acgagtcaag ggcctgatgg gcaagaagtt attcatcctg cttcttccat tctcacttgt       300
atctgttttc acgtctga                                                      318
```

<210> SEQ ID NO 4
<211> LENGTH: 105
<212> TYPE: PRT
<213> ORGANISM: Puccinia polysora

<400> SEQUENCE: 4

```
Met Ile Pro Thr Asp Cys Gly Ser Val Ser Gly Arg Cys Leu Ser Leu
1               5                   10                  15

Leu Leu Leu Arg Thr Cys Leu Arg Pro Cys Ile Ile Arg Leu Asp Pro
            20                  25                  30

Phe Pro Thr Gln Leu Val Leu Ile Pro Ser Pro Ser Ala Ser Ser Asn
        35                  40                  45

Ser Ser Ser Pro Val Ile Thr Ser Ser Pro Pro Thr Phe Ser Pro Phe
    50                  55                  60

Ala Ser Leu Pro Leu Ser Cys Phe Leu Leu Asp Val Ser Ala Asp Pro
65                  70                  75                  80
```

-continued

```
Thr Ser Gln Gly Pro Asp Gly Gln Glu Val Ile His Pro Ala Ser Ser
            85                  90                  95

Ile Leu Thr Cys Ile Cys Phe His Val
            100                 105

<210> SEQ ID NO 5
<211> LENGTH: 10
<212> TYPE: PRT
<213> ORGANISM: Puccinia polysora

<400> SEQUENCE: 5

Met Ile Pro Thr Asp Cys Gly Ser Val Ser
1               5                   10
```

PLANT PATHOGEN EFFECTOR AND DISEASE RESISTANCE GENE IDENTIFICATION, COMPOSITIONS, AND METHODS OF USE

CROSS-REFERENCE TO RELATED APPLICATIONS

This application is a national stage entry under 35 USC § 371 (b) of PCT/CN2022/084239, filed on Mar. 31, 2022, which claims the benefit of Chinese Patent Application No. 202110403600.2, filed Apr. 16, 2021, both of which are hereby incorporated herein in their entirety by reference.

FIELD

The compositions and methods are related to plant breeding and methods of identifying and selecting disease resistance genes and plant pathogen effector genes. Provided are methods to identify novel genes that encode plant pathogen effector proteins and proteins providing plant resistance to various diseases and uses thereof. These disease resistant genes are useful in the production of resistant plants through breeding, transgenic modification, or genome editing.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of RTS22031_SeqList.txt, a creation date of Feb. 25, 2021, and a size of 14 kb. The sequence listing filed via EFS-Web is part of the specification and is hereby incorporated in its entirety by reference herein.

BACKGROUND

Much work has been done on the mechanisms of disease resistance in plants. Some mechanisms of resistance are non-pathogen specific in nature, or so-called "non-host resistance." These may be based on cell wall structure or similar protective mechanisms. However, while plants lack an immune system with circulating antibodies and the other attributes of a mammalian immune system, they do have other mechanisms to specifically protect against pathogens. The most important and best studied of these are the plant disease resistance genes, or "R genes." One of very many reviews of this resistance mechanism and the R genes can be found in Bekhadir et al., (2004), *Current Opinion in Plant Biology* 7:391-399. There are 5 recognized classes of R genes: intracellular proteins with a nucleotide-binding site (NBS or NB-ARC) and a leucine-rich repeat (LRR); transmembrane proteins with an extracellular LRR domain (TM-LRR); transmembrane and extracellular LRR with a cytoplasmic kinase domain (TM-CK-LRR); membrane signal anchored protein with a coiled-coil cytoplasmic domain (MSAP-CC); and membrane or wall associated kinases with an N-terminal myristylation site (MAK-N or WAK) (See, for example: Cohn, et al., (2001), *Immunology*, 13:55-62; Dangl, et al. (2001), *Nature*, 411:826-833). There is a continuous need for disease-resistant plants and methods to find disease resistant genes, therefore, there is a need for a faster method of identification of disease resistance genes with greater throughput.

SUMMARY

Compositions and methods useful in identifying and selecting plant disease resistance genes, or "R genes," are provided herein. The compositions and methods are useful in selecting resistant plants, creating transgenic resistant plants, and/or creating resistant genome edited plants. Plants having newly conferred or enhanced resistance various plant diseases as compared to control plants are also provided herein.

In some embodiments, a maize or soybean protoplast comprises a predicted pathogen effector gene, a luciferase gene, and a potential maize disease resistance gene, wherein the predicted pathogen effector gene is predicted from a computational analysis. Optionally, the predicted pathogen effector gene and the luciferase reporter gene are both expressed from a single expression vector. In another embodiment, a plant comprises a dsRNA targeting a pathogen effector protein, wherein the pathogen effector protein was identified or validated through a luciferase reporter protoplast assay. In some embodiments, a protoplast comprises as plant pathogen effector comprising an amino acid sequence of at least 95% sequence identity, when compared to SEQ ID NO: 4.

In some embodiments, a plant pathogen effector comprises a polynucleotide operably linked to at least one regulatory sequence wherein said polynucleotide comprises a nucleic acid sequence encoding an amino acid sequence of at least 90% or at least 95% sequence identity, when compared to SEQ ID NO: 4. In some embodiments, the polynucleotide encoding SEQ ID NO: 4 comprises a nucleic acid sequence having at least 95% sequence identity to SEQ ID NO: 1, 2, or 3.

In some embodiments, a method of validating a causal disease resistance gene comprising a) identifying at least one potential gene in a disease resistance loci; b) transfecting a potential resistant gene from the disease resistance loci, a plant pathogen effector gene, and a luciferase gene into a maize protoplast, wherein the maize protoplast is derived from a maize plant susceptible to the plant pathogen; c) measuring luciferase activity; and d) selecting a gene that produces a hypersensitive response in the presence of the plant pathogen effector, wherein the plant pathogen effector gene encodes a pathogen effector as set forth in SEQ ID NO: 4.

In some embodiments, a method of validating a causal disease resistance gene comprising a) identifying at least one potential gene in a disease resistance loci in a disease resistance plant; b) transfecting at least one allele of a plant pathogen effector gene and a luciferase gene into a maize protoplast, wherein the maize protoplast is derived from the disease resistance plant; c) measuring luciferase activity; d) selecting a plant that produces luciferase activity in the presence of the effector gene and luciferase reporter gene; e) transfecting a potential resistant gene from the disease resistance loci of the disease resistant plant, a plant pathogen effector gene, and a luciferase gene into a maize protoplast, wherein the maize protoplast is derived from a maize plant susceptible to the plant pathogen; f) measuring luciferase activity; and g) selecting a gene that produces a hypersensitive response in the presence of the plant pathogen effector. In some embodiments, the plant pathogen effector gene encodes a pathogen effector as set forth in SEQ ID NO: 4. In another embodiment, disease resistant donor plant is a maize plant or a soybean plant.

In some embodiments, a method of selecting a disease resistant donor plant comprising a) transfecting at least one allele of a plant pathogen effector gene and a luciferase gene into a maize protoplast, wherein the maize protoplast is derived from a plant resistant to the plant pathogen; b) measuring luciferase activity; and c) selecting a maize plant that produces a hypersensitive response in the presence of the plant pathogen effector. In some embodiments, the plant pathogen effector gene encodes a pathogen effector as set forth in SEQ ID NO: 4. In another embodiment, disease resistant donor plant is a maize plant or a soybean plant.

In some embodiments, a method to identify homologous plant pathogen effectors comprising a) transfecting first allele of a plant pathogen effector gene and a luciferase gene into a maize protoplast; b) measuring luciferase activity; c) selecting a maize plant that produces a hypersensitive response in the presence of the plant pathogen effector; d) transfecting a second allele of a plant pathogen effector and a luciferase gene into a selected maize plant derived protoplast; and e) measuring luciferase activity. In some embodiments, the maize protoplast is derived from a disease resistant maize plant. In further embodiment, the method comprises transfecting at least one more different allele of a plant pathogen effector and a luciferase reporter gene into the selected maize protoplast. In some embodiments, the second allele of a plant pathogen effector was identified from a field population of plant pathogens, or the second allele of a plant pathogen effector indicates the increase in resistance in a field, wherein a pathogen effector comprises SEQ ID NO: 4.

In some embodiments, a method of breeding a plant for disease resistance comprising a) transfecting at least one allele of a plant pathogen effector gene and a luciferase gene into a maize protoplast, wherein the maize protoplast is derived from at least one maize plant resistant to the plant pathogen; b) measuring luciferase activity; c) Selecting a maize plant that produces a hypersensitive response in the presence of the plant pathogen effector. In further embodiment, the method comprises crossing the selected maize plant with a second maize plant. In some embodiments, the second allele of a plant pathogen effector was identified from a field population of plant pathogens, or the second allele of a plant pathogen effector indicates the increase in resistance in a field, wherein a pathogen effector comprises SEQ ID NO: 4.

In some embodiments, a method to monitor effectiveness of a disease resistance gene comprising a) transfecting a plant pathogen effector gene from a field derived pathogen strain and a luciferase gene into a maize protoplast, wherein the maize protoplast is derived from at least one maize plant resistant to the plant pathogen; b) measuring luciferase activity; c) transfecting a second allele of the plant pathogen effector gene from the same field derived pathogen strains and a luciferase reporter gene into the maize protoplast; d) measuring luciferase activity; and e) comparing luciferase activity from the first and second plant pathogen effector gene alleles, wherein a plant pathogen effector comprises SEQ ID NO: 4.

In some embodiments, a method to identify non-host resistance genes comprising a) transfecting at least one plant pathogen effector gene and a luciferase gene into a non-host protoplast, wherein the non-host protoplast is derived from at least one plant that shows no phenotypic changes in response to the plant pathogen; b) measuring luciferase activity; and c) selecting a non-host plant that has a protoplast that produces a hypersensitive response in the presence of the plant pathogen effector. In further embodiment, the method comprises identifying a causal gene for the non-host resistance to the plant pathogen effector as set forth in SEQ ID NO: 4.

DESCRIPTION OF THE SEQUENCE LISTING

Figure 1:
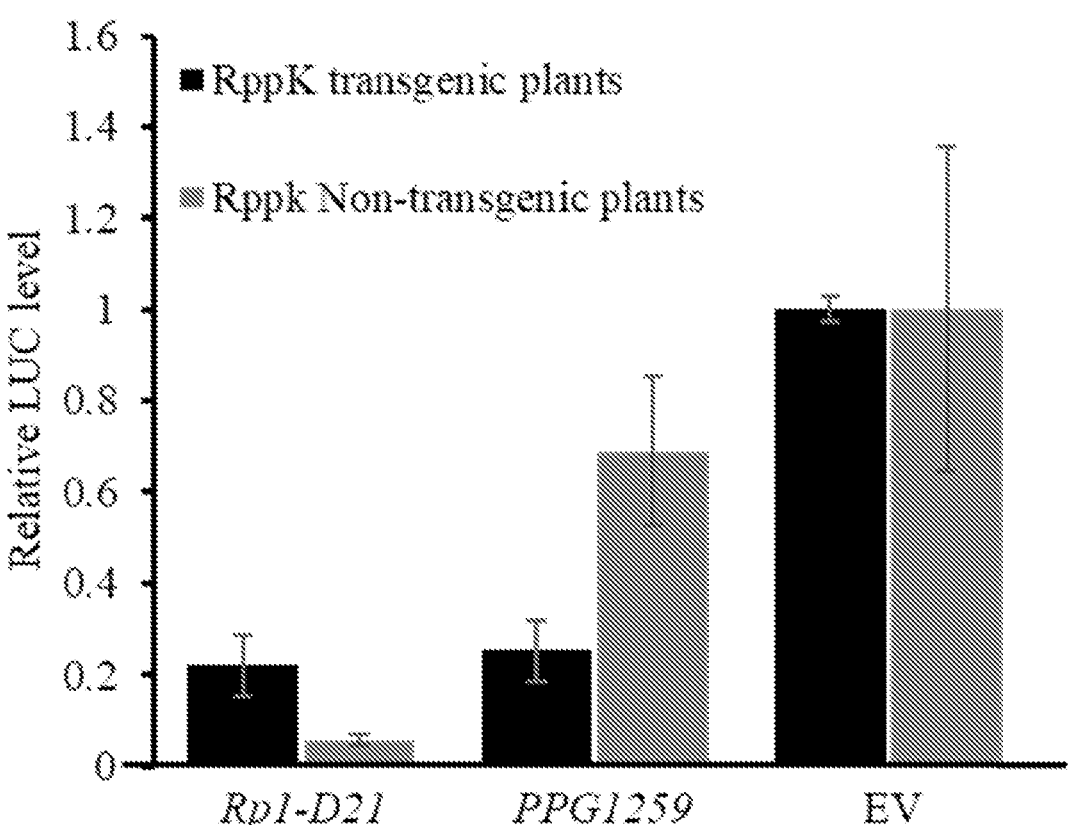
FIG. 1 shows expression of PPG1259 in protoplasts from Rppk transgenic plants induces HR.

| SEQ ID NO: | Sequence Description |
| --- | --- |
| 1 | PPG1259 genomic DNA sequence |
| 2 | PPG1259 cDNA sequence |
| 3 | PPG1259 CDS |
| 4 | PPG1259 protein sequence |
| 5 | PPG1259 protein signal peptide sequence |

DETAILED DESCRIPTION

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof, and so forth. All technical and scientific terms used herein have the same meaning as commonly understood to one of ordinary skill in the art to which this disclosure belongs unless clearly indicated otherwise.

For successful colonization or infection of host plants, plant pathogens must block host defenses or immune responses. The first line of defense in the plant immune system is a basal defense response that is triggered by pathogen-associated molecular patterns (PAMPs), conserved molecular features among pathogens (e.g. chitin for fungi). PAMP-triggered immunity (PTI) involves cell surface pattern recognition receptors (PRRs). Pathogens secrete effectors, which are generally small unique protein with no known functions, to modulate host cell physiology, suppress PTI and promote susceptibility. In turn, plants have developed a second line of defense, effector-triggered immunity (ETI), which involves the detection of specific avirulence effectors by intracellular receptors. These intracellular immune receptors are nucleotide-binding domain and leucine-rich repeat (NLR) proteins. NLRs recognize their cognate effectors either through direct interaction or through indirect detection. This recognition usually triggers the hypersensitive response (HR), a programmed cell death and the hallmark of ETI.

The NBS-LRR ("NLR") group of R-genes is the largest class of R-genes discovered to date. In Arabidopsis thaliana, over 150 are predicted to be present in the genome (Meyers, et al., (2003), Plant Cell, 15:809-834; Monosi, et al., (2004), Theoretical and Applied Genetics, 109:1434-1447), while in rice, approximately 500 NLR genes have been predicted (Monosi, (2004) supra). The NBS-LRR class of R genes is comprised of two subclasses. Class 1 NLR genes contain a TIR-Toll/Interleukin-1 like domain at their N' terminus; which to date have only been found in dicots (Meyers, (2003) supra; Monosi, (2004) supra). The second class of NBS-LRR contain either a coiled-coil domain or an (nt) domain at their N terminus (Bai, et al. (2002) Genome Research, 12:1871-1884; Monosi, (2004) supra; Pan, et al., (2000), Journal of Molecular Evolution, 50:203-213). Class 2 NBS-LRR have been found in both dicot and monocot species. (Bai, (2002) supra; Meyers, (2003) supra; Monosi, (2004) supra; Pan, (2000) supra).

The NBS domain of the gene appears to have a role in signaling in plant defense mechanisms (van der Biezen, et al., (1998), Current Biology: CB, 8: R226-R227). The LRR region appears to be the region that interacts with the pathogen AVR products (Michelmore, et al., (1998), Genome Res., 8:1113-1130; Meyers, (2003) supra). This LRR region in comparison with the NB-ARC (NBS) domain is under a much greater selection pressure to diversify (Michelmore, (1998) supra; Meyers, (2003) supra; Palomino, et al., (2002), Genome Research, 12:1305-1315). LRR domains are found in other contexts as well; these 20-29-residue motifs are present in tandem arrays in a number of proteins with diverse functions, such as hormone-receptor interactions, enzyme inhibition, cell adhesion and cellular trafficking. A number of recent studies revealed the involvement of LRR proteins in early mammalian development, neural development, cell polarization, regulation of gene expression and apoptosis signaling.

A resistance gene of the embodiments of the present disclosure encodes a novel R gene. The most numerous R genes correspond to the NBS-LRR type. There have also been many identified WAK type R genes. While multiple NBS-LRR genes have been described, they may differ widely in their response to different pathogens and exact action.

Positional cloning (or map-based cloning) has been the major method in identifying causal genes responsible for variations in disease resistance. In this approach, a resistance line is crossed to a susceptible line to generate a mapping population segregating for resistance and susceptibility. Linkage mapping is performed with genotyping and phenotyping data to detect disease QTL (Quantitative Trait Loci), or a disease resistance loci. A major disease QTL is "mendenlized" through back-crossing to the susceptible parents and validated. A validated QTL is then fine mapped into a small interval with a large segregating population (typically with over 3000 individuals). Sequences covering the QTL interval are obtained from the resistance line via BAC clone identification/sequencing or genome sequencing. The genome sequence is annotated, candidate genes identified and tested in transgenic plants. The candidate gene conferring resistance in transgenic plants is the causal gene underlying the disease QTL.

As used to herein, "disease resistant" or "have resistance to a disease" refers to a plant showing increase resistance to a disease compared to a control plant, which is a susceptible plant. Disease resistance may manifest in fewer and/or smaller lesions, increased plant health, increased yield, increased root mass, increased plant vigor, less or no discoloration, increased growth, reduced necrotic area, or reduced wilting.

Disease affecting maize plants include, but are not limited to, bacterial leaf blight and stalk rot; bacterial leaf spot; bacterial stripe; chocolate spot; goss's bacterial wilt and blight; holcus spot; purple leaf sheath; seed rot-seedling blight; bacterial wilt; corn stunt; anthracnose leaf blight; anthracnose stalk rot; aspergillus ear and kernel rot; banded leaf and sheath spot; black bundle disease; black kernel rot; borde blanco; brown spot; black spot; stalk rot; cephalosporium kernel rot; charcoal rot; corticium ear rot; curvularia leaf spot; didymella leaf spot; diplodia ear rot and stalk rot; diplodia ear rot; seed rot; corn seedling blight; diplodia leaf spot or leaf streak; downy mildews; brown stripe downy mildew; crazy top downy mildew; green ear downy mildew; graminicola downy mildew; java downy mildew; philippine downy mildew; sorghum downy mildew; spontaneum downy mildew; sugarcane downy mildew; dry ear rot; ergot; horse's tooth; corn eyespot; fusarium ear and stalk rot; fusarium blight; seedling root rot; gibberella ear and stalk rot; gray ear rot; gray leaf spot; cercospora leaf spot; helminthosporium root rot; hormodendrum ear rot; cladosporium rot; hyalothyridium leaf spot; late wilt; northern leaf blight; white blast; crown stalk rot; corn stripe; northern leaf spot; helminthosporium ear rot; penicillium ear rot; corn blue eye; blue mold; phaeocytostroma stalk rot and root rot; phaeosphaeria leaf spot; physalospora ear rot; botryosphaeria ear rot; pyrenochaeta stalk rot and root rot; pythium root rot; pythium stalk rot; red kernel disease; rhizoctonia ear rot; sclerotial rot; rhizoctonia root rot and stalk rot; rostratum leaf spot; common corn rust; southern corn rust; tropical corn rust; sclerotium ear rot; southern blight; selenophoma leaf spot; sheath rot; shuck rot; silage mold; common smut; false smut; head smut; southern corn leaf blight and stalk rot; southern leaf spot; tar spot; trichoderma ear rot and root rot; white ear rot, root and stalk rot; yellow leaf blight; zonate leaf spot; american wheat striate (wheat striate mosaic); barley stripe mosaic; barley yellow dwarf; brome mosaic; cereal chlorotic mottle; lethal necrosis (maize lethal necrosis disease); cucumber mosaic; johnsongrass mosaic; maize bushy stunt; maize chlorotic dwarf; maize chlorotic mottle; maize dwarf mosaic; maize leaf fleck; maize pellucid ringspot; maize rayado fino; maize red leaf and red stripe; maize red stripe; maize ring mottle; maize rough dwarf; maize sterile stunt; maize streak; maize stripe; maize tassel abortion; maize vein enation; maize wallaby ear; maize white leaf; maize white line mosaic; millet red leaf; and northern cereal mosaic.

Disease affecting rice plants include, but are not limited to, bacterial blight; bacterial leaf streak; foot rot; grain rot; sheath brown rot; blast; brown spot; crown sheath rot; downy mildew; eyespot; false smut; kernel smut; leaf smut; leaf scald; narrow brown leaf spot; root rot; seedling blight; sheath blight; sheath rot; sheath spot; alternaria leaf spot; and stem rot.

Disease affecting soybean plants include, but are not limited to, alternaria leaf spot; anthracnose; black leaf blight; black root rot; brown spot; brown stem rot; charcoal rot; choanephora leaf blight; downy mildew; drechslera blight; frogeye leaf spot; leptosphaerulina leaf spot; mycoleptodiscus root rot; neocosmospora stem rot; phomopsis seed decay; phytophthora root and stem rot; phyllosticta leaf spot; phymatotrichum root rot; pod and stem blight; powdery mildew; purple seed stain; pyrenochaeta leaf spot; pythium rot; red crown rot; dactuliophora leaf spot; rhizoctonia aerial blight; rhizoctonia root and stem rot; rust; scab; sclerotinia stem rot; sclerotium blight; stem canker; stemphylium leaf blight; sudden death syndrome; target spot; yeast spot; lance nematode; lesion nematode; pin nematode; reniform nematode; ring nematode; root-knot nematode; sheath nematode; cyst nematode; spiral nematode; sting nematode; stubby root nematode; stunt nematode; alfalfa mosaic; bean pod mottle; bean yellow mosaic; brazilian bud blight; chlorotic mottle; yellow mosaic; peanut mottle; peanut stripe; peanut stunt; chlorotic mottle; crinkle leaf; dwarf; severe stunt; and tobacco ringspot or bud blight.

Disease affecting canola plants include, but are not limited to, bacterial black rot; bacterial leaf spot; bacterial pod rot; bacterial soft rot; scab; crown gall; alternaria black spot; anthracnose; black leg; black mold rot; black root; brown girdling root rot; cercospora leaf spot; clubroot; downy mildew; fusarium wilt; gray mold; head rot; leaf spot; light leaf spot; pod rot; powdery mildew; ring spot; root rot; sclerotinia stem rot; seed rot, damping-off; root gall smut; southern blight; verticillium wilt; white blight; white leaf spot; staghead; yellows; crinkle virus; mosaic virus; yellows virus;

Disease affecting sunflower plants include, but are not limited to, apical chlorosis; bacterial leaf spot; bacterial wilt; crown gall; erwinia stalk rot and head rot; lternaria leaf blight, stem spot and head rot; botrytis head rot; charcoal rot; downy mildew; fusarium stalk rot; fusarium wilt; myrothecium leaf and stem spot; phialophora yellows; phoma black stem; phomopsis brown stem canker; phymatotrichum root rot; phytophthora stem rot; powdery mildew; pythium seedling blight and root rot; rhizoctonia seedling blight; rhizopus head rot; sunflower rust; sclerotium basal stalk and root rot; septoria leaf spot; verticillium wilt; white rust; yellow rust; dagger; pin; lesion; reniform; root knot; and chlorotic mottle;

Disease affecting sorghum plants include, but are not limited to, bacterial leaf spot; bacterial leaf streak; bacterial leaf stripe; acremonium wilt; anthracnose; charcoal rot; crazy top downy mildew; damping-off and seed rot; ergot; fusarium head blight, root and stalk rot; grain storage mold; gray leaf spot; latter leaf spot; leaf blight; milo disease; oval leaf spot; pokkah boeng; pythium root rot; rough leaf spot; rust; seedling blight and seed rot; smut, covered kernel; smut, head; smut, loose kernel; sooty stripe; downy mildew; tar spot; target leaf spot; and zonate leaf spot and sheath blight.

A plant having disease resistance may have 5, 10, 15, 20, 25, 30, 35, 40, 45, 50, 55, 60, 65, 70, 75, 80, 85, 90, 95, or 100% increased resistance to a disease compared to a control plant. In some embodiments, a plant may have 5, 10, 15, 20, 25, 30, 35, 40, 45, 50, 55, 60, 65, 70, 75, 80, 85, 90, 95, or 100% increased plant health in the presence of a disease compared to a control plant As used herein, the term "clustering" or "clustering approach" means pooling and clustering sequences in a location-agnostic manner using a nearest neighbor joining algorithm, hierarchical clustering such as Ward's method, a maximum likelihood method, or any other clustering algorithm or method.

The term "crossed" or "cross" refers to a sexual cross and involved the fusion of two haploid gametes via pollination to produce diploid progeny (e.g., cells, seeds or plants). The term encompasses both the pollination of one plant by another and selfing (or self-pollination, e.g., when the pollen and ovule are from the same plant).

An "elite line" is any line that has resulted from breeding and selection for superior agronomic performance.

An "exotic strain," a "tropical line," or an "exotic germplasm" is a strain derived from a plant not belonging to an available elite line or strain of germplasm. In the context of a cross between two plants or strains of germplasm, an exotic germplasm is not closely related by descent to the elite germplasm with which it is crossed. Most commonly, the exotic germplasm is not derived from any known elite line, but rather is selected to introduce novel genetic elements (typically novel alleles) into a breeding program.

A "favorable allele" is the allele at a particular locus (a marker, a QTL, a gene etc.) that confers, or contributes to, an agronomically desirable phenotype, e.g., disease resistance, and that allows the identification of plants with that agronomically desirable phenotype. A favorable allele of a marker is a marker allele that segregates with the favorable phenotype.

"Genetic markers" are nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

"Germplasm" refers to genetic material of or from an individual (e.g., a plant), a group of individuals (e.g., a plant line, variety or family), or a clone derived from a line, variety, species, or culture, or more generally, all individuals within a species or for several species (e.g., maize germplasm collection or Andean germplasm collection). The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, that can be cultured into a whole plant.

A "haplotype" is the genotype of an individual at a plurality of genetic loci, i.e. a combination of alleles. Typically, the genetic loci described by a haplotype are physically and genetically linked, i.e., on the same chromosome segment.

The term "heterogeneity" is used to indicate that individuals within the group differ in genotype at one or more specific loci.

The heterotic response of material, or "heterosis", can be defined by performance which exceeds the average of the parents (or high parent) when crossed to other dissimilar or unrelated groups.

A "heterotic group" comprises a set of genotypes that perform well when crossed with genotypes from a different heterotic group (Hallauer et al. (1998) Corn breeding, p. 463-564. In G. F. Sprague and J. W. Dudley (ed.) Corn and corn improvement). Inbred lines are classified into heterotic groups, and are further subdivided into families within a heterotic group, based on several criteria such as pedigree, molecular marker-based associations, and performance in hybrid combinations (Smith et al. (1990) Theor. Appl. Gen. 80:833-840). The two most widely used heterotic groups in the United States are referred to as "Iowa Stiff Stalk Synthetic" (also referred to herein as "stiff stalk") and "Lancaster" or "Lancaster Sure Crop" (sometimes referred to as NSS, or non-Stiff Stalk).

Some heterotic groups possess the traits needed to be a female parent, and others, traits for a male parent. For example, in maize, yield results from public inbreds released from a population called BSSS (Iowa Stiff Stalk Synthetic population) has resulted in these inbreds and their derivatives becoming the female pool in the central Corn Belt. BSSS inbreds have been crossed with other inbreds, e.g. SD 105 and Maiz Amargo, and this general group of materials has become known as Stiff Stalk Synthetics (SSS) even though not all of the inbreds are derived from the original BSSS population (Mikel and Dudley (2006) *Crop Sci:* 46:1193-1205). By default, all other inbreds that combine well with the SSS inbreds have been assigned to the male pool, which for lack of a better name has been designated as NSS, i.e. Non-Stiff Stalk. This group includes several major heterotic groups such as Lancaster Surecrop, Iodent, and Leaming Corn.

The term "homogeneity" indicates that members of a group have the same genotype at one or more specific loci.

The term "hybrid" refers to the progeny obtained between the crossing of at least two genetically dissimilar parents.

The term "inbred" refers to a line that has been bred for genetic homogeneity.

The term "indel" refers to an insertion or deletion, wherein one line may be referred to as having an inserted nucleotide or piece of DNA relative to a second line, or the second line may be referred to as having a deleted nucleotide or piece of DNA relative to the first line.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., detected by a marker that is associated with a phenotype, at a QTL, a transgene, or the like. In any case, offspring comprising the desired allele can be repeatedly backcrossed to a line having a desired genetic background and selected for the desired allele, to result in the allele becoming fixed in a selected genetic background.

The process of "introgressing" is often referred to as "backcrossing" when the process is repeated two or more times.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor.

As used herein, the term "linkage" is used to describe the degree with which one marker locus is associated with another marker locus or some other locus. The linkage relationship between a molecular marker and a locus affecting a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM) of a single meiosis map (a genetic map based on a population that has undergone one round of meiosis, such as e.g. an $F_2$; the IBM2 maps consist of multiple meiosis). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "in proximity to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 CM or less from each other.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency. Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same linkage group.) As used herein, linkage can be between two markers, or alternatively between a marker and a locus affecting a phenotype. A marker locus can be "associated with" (linked to) a trait. The degree of linkage of a marker locus and a locus affecting a phenotypic trait is measured, e.g., as a statistical probability of co-segregation of that molecular marker with the phenotype (e.g., an F statistic or LOD score).

Linkage disequilibrium is most commonly assessed using the measure $r^2$, which is calculated using the formula described by Hill, W. G. and Robertson, A, Theor. Appl. Genet. 38:226-231(1968). When $r^2=1$, complete LD exists between the two marker loci, meaning that the markers have not been separated by recombination and have the same allele frequency. The r' value will be dependent on the population used. Values for $r^2$ above ⅓ indicate sufficiently strong LD to be useful for mapping (Ardlie et al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome, e.g. where a nucleotide, gene, sequence, or marker is located.

The "logarithm of odds (LOD) value" or "LOD score" (Risch, *Science* 255:803-804 (1992)) is used in genetic interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage. LOD scores can also be used to show the strength of association between marker loci and quantitative traits in "quantitative trait loci" mapping. In this case, the LOD score's size is dependent on the closeness of the marker locus to the locus affecting the quantitative trait, as well as the size of the quantitative trait effect.

The term "plant" includes whole plants, plant cells, plant protoplast, plant cell or tissue culture from which plants can be regenerated, plant calli, plant clumps and plant cells that are intact in plants or parts of plants, such as seeds, flowers, cotyledons, leaves, stems, buds, roots, root tips and the like. As used herein, a "modified plant" means any plant that has a genetic change due to human intervention. A modified plant may have genetic changes introduced through plant transformation, genome editing, or conventional plant breeding A "marker" is a means of finding a position on a genetic or physical map, or else linkages among markers and trait loci (loci affecting traits). The position that the marker detects may be known via detection of polymorphic alleles and their genetic mapping, or else by hybridization, sequence match or amplification of a sequence that has been physically mapped. A marker can be a DNA marker (detects DNA polymorphisms), a protein (detects variation at an encoded polypeptide), or a simply inherited phenotype (such as the 'waxy' phenotype). A DNA marker can be developed from genomic nucleotide sequence or from expressed nucleotide sequences (e.g., from a spliced RNA or a cDNA).

Depending on the DNA marker technology, the marker will consist of complementary primers flanking the locus and/or complementary probes that hybridize to polymorphic alleles at the locus. A DNA marker, or a genetic marker, can also be used to describe the gene, DNA sequence or nucleotide on the chromosome itself (rather than the components used to detect the gene or DNA sequence) and is often used when that DNA marker is associated with a particular trait in human genetics (e.g. a marker for breast cancer). The term marker locus is the locus (gene, sequence or nucleotide) that the marker detects.

Markers that detect genetic polymorphisms between members of a population are well-established in the art. Markers can be defined by the type of polymorphism that they detect and also the marker technology used to detect the polymorphism. Marker types include but are not limited to, e.g., detection of restriction fragment length polymorphisms (RFLP), detection of isozyme markers, randomly amplified polymorphic DNA (RAPD), amplified fragment length polymorphisms (AFLPs), detection of simple sequence repeats (SSRs), detection of amplified variable sequences of the plant genome, detection of self-sustained sequence replication, or detection of single nucleotide polymorphisms (SNPs). SNPs can be detected e.g. via DNA sequencing, PCR-based sequence specific amplification methods, detection of polynucleotide polymorphisms by allele specific hybridization (ASH), dynamic allele-specific hybridization (DASH), molecular beacons, microarray hybridization, oligonucleotide ligase assays, Flap endonucleases, 5' endonucleases, primer extension, single strand conformation polymorphism (SSCP) or temperature gradient gel electrophoresis (TGGE). DNA sequencing, such as the pyrosequencing technology has the advantage of being able to detect a series of linked SNP alleles that constitute a haplotype. Haplotypes tend to be more informative (detect a higher level of polymorphism) than SNPs.

A "marker allele", alternatively an "allele of a marker locus", can refer to one of a plurality of polymorphic nucleotide sequences found at a marker locus in a population.

"Marker assisted selection" (of MAS) is a process by which individual plants are selected based on marker genotypes.

"Marker assisted counter-selection" is a process by which marker genotypes are used to identify plants that will not be selected, allowing them to be removed from a breeding program or planting.

A "marker haplotype" refers to a combination of alleles at a marker locus.

A "marker locus" is a specific chromosome location in the genome of a species where a specific marker can be found. A marker locus can be used to track the presence of a second linked locus, e.g., one that affects the expression of a phenotypic trait. For example, a marker locus can be used to monitor segregation of alleles at a genetically or physically linked locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

An allele "negatively" correlates with a trait when it is linked to it and when presence of the allele is an indicator that a desired trait or trait form will not occur in a plant comprising the allele.

The term "phenotype", "phenotypic trait", or "trait" can refer to the observable expression of a gene or series of genes. The phenotype can be observable to the naked eye, or by any other means of evaluation known in the art, e.g., weighing, counting, measuring (length, width, angles, etc.), microscopy, biochemical analysis, or an electromechanical assay. In some cases, a phenotype is directly controlled by a single gene or genetic locus, i.e., a "single gene trait" or a "simply inherited trait". In the absence of large levels of environmental variation, single gene traits can segregate in a population to give a "qualitative" or "discrete" distribution, i.e. the phenotype falls into discrete classes. In other cases, a phenotype is the result of several genes and can be considered a "multigenic trait" or a "complex trait". Multigenic traits segregate in a population to give a "quantitative" or "continuous" distribution, i.e. the phenotype cannot be separated into discrete classes. Both single gene and multigenic traits can be affected by the environment in which they are being expressed, but multigenic traits tend to have a larger environmental component.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination (that can vary in different populations).

A "polymorphism" is a variation in the DNA between two or more individuals within a population. A polymorphism preferably has a frequency of at least 1% in a population. A useful polymorphism can include a single nucleotide polymorphism (SNP), a simple sequence repeat (SSR), or an insertion/deletion polymorphism, also referred to herein as an "indel".

A "production marker" or "production SNP marker" is a marker that has been developed for high-throughput purposes. Production SNP markers are developed to detect specific polymorphisms and are designed for use with a variety of chemistries and platforms.

The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question.

A "reference sequence" or a "consensus sequence" is a defined sequence used as a basis for sequence comparison. The reference sequence for a marker is obtained by sequencing a number of lines at the locus, aligning the nucleotide sequences in a sequence alignment program (e.g. Sequencher), and then obtaining the most common nucleotide sequence of the alignment. Polymorphisms found among the individual sequences are annotated within the consensus sequence. A reference sequence is not usually an exact copy of any individual DNA sequence, but represents an amalgam of available sequences and is useful for designing primers and probes to polymorphisms within the sequence.

An "unfavorable allele" of a marker is a marker allele that segregates with the unfavorable plant phenotype, therefore providing the benefit of identifying plants that can be removed from a breeding program or planting.

The term "yield" refers to the productivity per unit area of a particular plant product of commercial value. Yield is affected by both genetic and environmental factors. "Agronomics", "agronomic traits", and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

Marker loci that demonstrate statistically significant co-segregation with a disease resistance trait that confers broad resistance against a specified disease or diseases are provided herein. Detection of these loci or additional linked loci and the resistance gene may be used in marker assisted selection as part of a breeding program to produce plants that have resistance to a disease or diseases.

Genetic Mapping

It has been recognized for quite some time that specific genetic loci correlating with particular phenotypes, such as disease resistance, can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or MAS).

A variety of methods well known in the art are available for detecting molecular markers or clusters of molecular markers that co-segregate with a trait of interest, such as a disease resistance trait. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference. Two such methods used to detect trait loci of interest are: 1) Population-based association analysis (i.e. association mapping) and 2) Traditional linkage analysis.

Association Mapping

Understanding the extent and patterns of linkage disequilibrium (LD) in the genome is a prerequisite for developing efficient association approaches to identify and map quantitative trait loci (QTL). Linkage disequilibrium (LD) refers to the non-random association of alleles in a collection of individuals. When LD is observed among alleles at linked loci, it is measured as LD decay across a specific region of a chromosome. The extent of the LD is a reflection of the recombinational history of that region. The average rate of LD decay in a genome can help predict the number and density of markers that are required to undertake a genome-wide association study and provides an estimate of the resolution that can be expected.

Association or LD mapping aims to identify significant genotype-phenotype associations. It has been exploited as a powerful tool for fine mapping in outcrossing species such as humans (Corder et al. (1994) "Protective effect of apolipoprotein-E type-2 allele for late-onset Alzheimer-disease," *Nat Genet* 7:180-184; Hastbacka et al. (1992) "Linkage disequilibrium mapping in isolated founder populations: diastrophic dysplasia in Finland," *Nat Genet* 2:204-211; Kerem et al. (1989) "Identification of the cystic fibrosis gene: genetic analysis," *Science* 245:1073-1080) and maize (Remington et al., (2001) "Structure of linkage disequilibrium and phenotype associations in the maize genome," *Proc Natl Acad Sci USA* 98:11479-11484; Thornsberry et al. (2001) "Dwarf8 polymorphisms associate with variation in flowering time," *Nat Genet* 28:286-289; reviewed by Flint-Garcia et al. (2003) "Structure of linkage disequilibrium in plants," *Annu Rev Plant Biol.* 54:357-374), where recombination among heterozygotes is frequent and results in a rapid decay of LD. In inbreeding species where recombination among homozygous genotypes is not genetically detectable, the extent of LD is greater (i.e., larger blocks of linked markers are inherited together) and this dramatically enhances the detection power of association mapping (Wall and Pritchard (2003) "Haplotype blocks and linkage disequilibrium in the human genome," *Nat Rev Genet* 4:587-597).

The recombinational and mutational history of a population is a function of the mating habit as well as the effective size and age of a population. Large population sizes offer enhanced possibilities for detecting recombination, while older populations are generally associated with higher levels of polymorphism, both of which contribute to observably accelerated rates of LD decay. On the other hand, smaller effective population sizes, e.g., those that have experienced a recent genetic bottleneck, tend to show a slower rate of LD decay, resulting in more extensive haplotype conservation (Flint-Garcia et al. (2003) "Structure of linkage disequilibrium in plants," *Annu Rev Plant Biol.* 54:357-374).

Elite breeding lines provide a valuable starting point for association analyses. Association analyses use quantitative phenotypic scores (e.g., disease tolerance rated from one to nine for each line) in the analysis (as opposed to looking only at tolerant versus resistant allele frequency distributions in intergroup allele distribution types of analysis). The availability of detailed phenotypic performance data collected by breeding programs over multiple years and environments for a large number of elite lines provides a valuable dataset for genetic marker association mapping analyses. This paves the way for a seamless integration between research and application and takes advantage of historically accumulated data sets. However, an understanding of the relationship between polymorphism and recombination is useful in developing appropriate strategies for efficiently extracting maximum information from these resources.

This type of association analysis neither generates nor requires any map data, but rather is independent of map position. This analysis compares the plants' phenotypic score with the genotypes at the various loci. Subsequently, any suitable map (for example, a composite map) can optionally be used to help observe distribution of the identified QTL markers and/or QTL marker clustering using previously determined map locations of the markers.

Traditional Linkage Analysis

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, Genetics 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

Marker loci that demonstrate statistically significant cosegregation with a disease resistance trait, as determined by traditional linkage analysis and by whole genome association analysis, are provided herein. Detection of these loci or additional linked loci can be used in marker assisted breeding programs to produce plants having disease resistance.

Activities in marker assisted breeding programs may include but are not limited to: selecting among new breeding populations to identify which population has the highest frequency of favorable nucleic acid sequences based on historical genotype and agronomic trait associations, selecting favorable nucleic acid sequences among progeny in breeding populations, selecting among parental lines based on prediction of progeny performance, and advancing lines in germplasm improvement activities based on presence of favorable nucleic acid sequences.

Markers and Linkage Relationships

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 CM, 7 CM, 6 CM, 5 CM, 4 CM, 3 CM, 2 cM, 1 CM, 0.75 cM, 0.5 CM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can co-segregate with the disease resistance trait, it is important to note that the marker locus is not necessarily responsible for the expression of the disease resistance phenotype. For example, it is not a requirement that the marker polynucleotide sequence be part of a gene that is responsible for the disease resistant phenotype (for example, is part of the gene open reading frame). The association between a specific marker allele and the disease resistance trait is due to the original "coupling" linkage phase between the marker allele and the allele in the ancestral line from which the allele originated. Eventually, with repeated recombination, crossing over events between the marker and genetic locus can change this orientation. For this reason, the favorable marker allele may change depending on the linkage phase that exists within the parent having resistance to the disease that is used to create segregating populations. This does not change the fact that the marker can be used to monitor segregation of the phenotype. It only changes which marker allele is considered favorable in a given segregating population.

Methods presented herein include detecting the presence of one or more marker alleles associated with disease resistance in a plant and then identifying and/or selecting plants that have favorable alleles at those marker loci. Markers have been identified herein as being associated with the disease resistance trait and hence can be used to predict disease resistance in a plant. Any marker within 50 cM, 40 cM, 30 CM, 20 cM, 15 CM, 10 cM, 9 CM, 8 CM, 7 CM, 6 CM, 5 CM, 4 CM, 3 CM, 2 cM, 1 cM, 0.75 cM, 0.5 cM or 0.25 CM (based on a single meiosis based genetic map) could also be used to predict disease resistance in a plant.

Marker Assisted Selection

Molecular markers can be used in a variety of plant breeding applications (e.g. see Staub et al. (1996) *Hortscience* 31: 729-741; Tanksley (1983) *Plant Molecular Biology Reporter.* 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. In some embodiments, the methods disclosed herein produce a marker in a disease resistance gene, wherein the gene was identified by inferring genomic location from clustering of conserved domains or a clustering analysis.

When a gene is introgressed by MAS, it is not only the gene that is introduced but also the flanking regions (Gepts. (2002). *Crop Sci;* 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite line. This is also sometimes referred to as "yield drag." The size of the flanking region can be decreased by additional backcrossing, although this is not always successful, as breeders do not have control over the size of the region or the recombination breakpoints (Young et al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The key components to the implementation of MAS are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) *Nucleic Acid Research* 17: 6463-6471; Wang et al. (1994) *Theoretical and Applied Genetics,* 88:1-6) Polymorphisms arise due to variation in the number of repeat units, probably caused by slippage during DNA replication (Levinson and Gutman (1987) *Mol Biol Evol* 4: 203-221). The variation in repeat length may be detected by designing PCR primers to the conserved non-repetitive flanking regions (Weber and May (1989) *Am J Hum Genet.* 44:388-396). SSRs are highly suited to mapping and MAS as they are multi-allelic, codominant, reproducible and amenable to high throughput automation (Rafalski et al. (1996) Generating and using DNA markers in plants. In: *Non-mammalian genomic analysis: a practical guide.* Academic press. pp 75-135).

Various types of SSR markers can be generated, and SSR profiles can be obtained by gel electrophoresis of the amplification products. Scoring of marker genotype is based on the size of the amplified fragment.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). *Plant Mol Biol* 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 *Plant Molecular Biology* 48:539-547). SNPs can be assayed at an even higher level of throughput than SSRs, in a so-called 'ultra-high-throughput' fashion, as SNPs do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing, and coded spheres. Such methods have been reviewed in: Gut (2001) *Hum Mutat* 17 pp. 475-492; Shi (2001) *Clin Chem* 47, pp. 164-172; Kwok (2000) *Pharmacogenomics* 1, pp. 95-100; and Bhattramakki and Rafalski (2001) Discovery and application of single nucleotide polymorphism markers in plants. In: R. J. Henry, Ed, *Plant Genotyping: The DNA Finger-printing of Plants*, CABI Publishing, Wallingford. A wide range of commercially available technologies utilize these and other methods to interrogate SNPs including Mass-code.™. (Qiagen), INVADER®. (Third Wave Technologies) and Invader PLUS®, SNAPSHOT®. (Applied Biosystems), TAQMAN®. (Applied Biosystems) and BEADARRAYS®. (Illumina).

A number of SNPs together within a sequence, or across linked sequences, can be used to describe a haplotype for any particular genotype (Ching et al. (2002), *BMC Genet.* 3:19 pp Gupta et al. 2001, Rafalski (2002b), *Plant Science* 162:329-333). Haplotypes can be more informative than single SNPs and can be more descriptive of any particular genotype. For example, a single SNP may be allele "T" for a specific line or variety with disease resistance, but the allele T' might also occur in the breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high through-put marker detection platforms known to those of ordinary skill in the art makes this process highly efficient and effective.

Many of the markers presented herein can readily be used as single nucleotide polymorphic (SNP) markers to select for the R gene. Using PCR, the primers are used to amplify DNA segments from individuals (preferably inbred) that represent the diversity in the population of interest. The PCR products are sequenced directly in one or both directions. The resulting sequences are aligned and polymorphisms are identified. The polymorphisms are not limited to single nucleotide polymorphisms (SNPs), but also include indels, CAPS, SSRs, and VNTRs (variable number of tandem repeats). Specifically, with respect to the fine map informa-tion described herein, one can readily use the information provided herein to obtain additional polymorphic SNPs (and other markers) within the region amplified by the primers disclosed herein. Markers within the described map region can be hybridized to BACs or other genomic libraries, or electronically aligned with genome sequences, to find new sequences in the same approximate location as the described markers.

In addition to SSR's, FLPs and SNPs, as described above, other types of molecular markers are also widely used, including but not limited to expressed sequence tags (ESTs), SSR markers derived from EST sequences, randomly ampli-fied polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) *Plant Molecular Biology Reporter* 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the species, or even across other species that have been geneti-cally or physically aligned.

In general, MAS uses polymorphic markers that have been identified as having a significant likelihood of co-segregation with a trait such as the disease resistance trait. Such markers are presumed to map near a gene or genes that give the plant its disease resistant phenotype, and are con-sidered indicators for the desired trait, or markers. Plants are tested for the presence of a desired allele in the marker, and plants containing a desired genotype at one or more loci are expected to transfer the desired genotype, along with a desired phenotype, to their progeny. Thus, plants with dis-ease resistance can be selected for by detecting one or more marker alleles, and in addition, progeny plants derived from those plants can also be selected. Hence, a plant containing a desired genotype in a given chromosomal region (i.e. a genotype associated with disease resistance) is obtained and then crossed to another plant. The progeny of such a cross would then be evaluated genotypically using one or more markers and the progeny plants with the same genotype in a given chromosomal region would then be selected as having disease resistance.

The SNPs could be used alone or in combination (i.e. a SNP haplotype) to select for a favorable resistant gene allele associated with the disease resistance.

The skilled artisan would expect that there might be additional polymorphic sites at marker loci in and around a chromosome marker identified by the methods disclosed herein, wherein one or more polymorphic sites is in linkage disequilibrium (LD) with an allele at one or more of the polymorphic sites in the haplotype and thus could be used in a marker assisted selection program to introgress a gene allele or genomic fragment of interest. Two particular alleles at different polymorphic sites are said to be in LD if the presence of the allele at one of the sites tends to predict the presence of the allele at the other site on the same chromo-some (Stevens, *Mol. Diag.* 4:309-17 (1999)). The marker loci can be located within 5 cM, 2 cM, or 1 cM (on a single meiosis based genetic map) of the disease resistance trait QTL.

The skilled artisan would understand that allelic fre-quency (and hence, haplotype frequency) can differ from one germplasm pool to another. Germplasm pools vary due to maturity differences, heterotic groupings, geographical distribution, etc. As a result, SNPs and other polymorphisms may not be informative in some germplasm pools.

Plant Compositions

Plants identified and/or selected by any of the methods described above are also of interest.

Proteins and Variants and Fragments Thereof

R gene polypeptides are encompassed by the disclosure. "R gene polypeptide" and "R gene protein" as used herein interchangeably refers to a polypeptide(s) having a disease resistance activity. A variety of R gene polypeptides and plant pathogen effectors are contemplated.

"Sufficiently identical" is used herein to refer to an amino acid sequence that has at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity. In some embodiments the sequence identity is against the full length sequence of a polypeptide. The term "about" when used herein in context with percent sequence identity means +/−1.0%.

A "recombinant protein" is used herein to refer to a protein that is no longer in its natural environment, for example in vitro or in a recombinant bacterial or plant host cell; a protein that is expressed from a polynucleotide that has been edited from its native version; or a protein that is expressed from a polynucleotide in a different genomic position relative to the native sequence.

"Substantially free of cellular material" as used herein refers to a polypeptide including preparations of protein having less than about 30%, 20%, 10% or 5% (by dry weight) of non-target protein (also referred to herein as a "contaminating protein").

"Fragments" or "biologically active portions" include polypeptide or polynucleotide fragments comprising sequences sufficiently identical to an R gene polypeptide or polynucleotide, respectively, and that exhibit disease resistance when expressed in a plant.

"Variants" as used herein refers to proteins or polypeptides having an amino acid sequence that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater identical to the parental amino acid sequence.

Methods for such manipulations are generally known in the art. For example, amino acid sequence variants of a polypeptide can be prepared by mutations in the DNA. This may also be accomplished by one of several forms of mutagenesis, such as for example site-specific double strand break technology, and/or in directed evolution. In some aspects, the changes encoded in the amino acid sequence will not substantially affect the function of the protein. Such variants will possess the desired activity. However, it is understood that the ability of an R gene polypeptide to confer disease resistance may be improved by the use of such techniques upon the compositions of this disclosure.

Nucleic Acid Molecules and Variants and Fragments Thereof

Isolated or recombinant nucleic acid molecules comprising nucleic acid sequences encoding R gene polypeptides or biologically active portions thereof, as well as nucleic acid molecules sufficient for use as hybridization probes to identify nucleic acid molecules encoding proteins with regions of sequence homology are provided. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule (or DNA) is used herein to refer to a nucleic acid sequence (or DNA) that is no longer in its natural environment, for example in vitro. A "recombinant" nucleic acid molecule (or DNA) is used herein to refer to a nucleic acid sequence (or DNA) that is in a recombinant bacterial or plant host cell; has been edited from its native sequence; or is located in a different location than the native sequence. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes. For example, in various embodiments, the recombinant nucleic acid molecules encoding R gene polypeptides can contain less than about 5 kb, 4 kb, 3 kb, 2 kb, 1 kb, 0.5 kb or 0.1 kb of nucleic acid sequences that naturally flank the nucleic acid molecule in genomic DNA of the cell from which the nucleic acid is derived.

In some embodiments an isolated nucleic acid molecule encoding R gene polypeptides has one or more change in the nucleic acid sequence compared to the native or genomic nucleic acid sequence. In some embodiments the change in the native or genomic nucleic acid sequence includes but is not limited to: changes in the nucleic acid sequence due to the degeneracy of the genetic code; changes in the nucleic acid sequence due to the amino acid substitution, insertion, deletion and/or addition compared to the native or genomic sequence; removal of one or more intron; deletion of one or more upstream or downstream regulatory regions; and deletion of the 5' and/or 3' untranslated region associated with the genomic nucleic acid sequence. In some embodiments the nucleic acid molecule encoding an R gene polypeptide is a non-genomic sequence.

A variety of polynucleotides that encode R gene polypeptides or related proteins are contemplated. Such polynucleotides are useful for production of R gene polypeptides in host cells when operably linked to a suitable promoter, transcription termination and/or polyadenylation sequences. Such polynucleotides are also useful as probes for isolating homologous or substantially homologous polynucleotides that encode R gene polypeptides or related proteins.

"Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments the nucleic acid molecule encoding the R gene polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a synthetic nucleic acid sequence.

Nucleic acid molecules that are fragments of these nucleic acid sequences encoding R gene polypeptides are also encompassed by the embodiments. "Fragment" as used herein refers to a portion of the nucleic acid sequence encoding an R gene polypeptide. A fragment of a nucleic acid sequence may encode a biologically active portion of an R gene polypeptide or it may be a fragment that can be used as a hybridization probe or PCR primer using methods disclosed below. Nucleic acid molecules that are fragments of a nucleic acid sequence encoding an R gene polypeptide comprise at least about 150, 180, 210, 240, 270, 300, 330, 360, 400, 450, or 500 contiguous nucleotides or up to the number of nucleotides present in a full-length nucleic acid sequence encoding a R gene polypeptide identified by the methods disclosed herein, depending upon the intended use. "Contiguous nucleotides" is used herein to refer to nucleotide residues that are immediately adjacent to one another. Fragments of the nucleic acid sequences of the embodiments will encode protein fragments that retain the biological activity of the R gene polypeptide and, hence, retain disease resistance. "Retains disease resistance" is used herein to refer to a polypeptide having at least about 10%, at least about 30%, at least about 50%, at least about 70%, 80%, 90%, 95% or higher of the disease resistance of the full-length R gene polypeptide.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

The embodiments also encompass nucleic acid molecules encoding R gene polypeptide variants. "Variants" of the R gene polypeptide encoding nucleic acid sequences include those sequences that encode the R gene polypeptides identified by the methods disclosed herein, but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis but which still encode the R gene polypeptides disclosed herein.

The skilled artisan will further appreciate that changes can be introduced by mutation of the nucleic acid sequences thereby leading to changes in the amino acid sequence of the encoded R gene polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Alternatively, variant nucleic acid sequences can be made by introducing mutations randomly along all or part of the coding sequence, such as by saturation mutagenesis, and the resultant mutants can be screened for ability to confer activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional polypeptide homologues and fragments thereof with desired properties. A variety of such reactions are known. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries and any recombinant polynucleotide produced by such methods. Additionally, such methods optionally comprise selecting a variant polynucleotide from such libraries based on activity, as is wherein such recursive recombination is done in vitro or in vivo.

A variety of diversity generating protocols, including nucleic acid recursive recombination protocols are available and fully described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods herein or otherwise available to one of skill, any nucleic acids that are produced can be selected for a desired activity or property, e.g. such activity at a desired pH, etc. This can include identifying any activity that can be detected, for example, in an automated or automatable format, by any of the assays in the art. A variety of related (or even unrelated) properties can be evaluated, in serial or in parallel, at the discretion of the practitioner.

The nucleotide sequences of the embodiments can also be used to isolate corresponding sequences from a different source. In this manner, methods such as PCR, hybridization, and the like can be used to identify such sequences based on their sequence homology to the sequences identified by the methods disclosed herein. Sequences that are selected based on their sequence identity to the entire sequences set forth herein or to fragments thereof are encompassed by the embodiments. Such sequences include sequences that are orthologs of the sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, New York), hereinafter "Sambrook". See also, Innis, et al., eds. (1990) *PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization methods, all or part of the nucleic acid sequence can be used to screen cDNA or genomic libraries. Methods for construction of such cDNA and genomic libraries are generally known in the art and are disclosed in Sambrook and Russell, (2001), supra. The so-called hybridization probes may be genomic DNA fragments, cDNA fragments, RNA fragments or other oligonucleotides and may be labeled with a detectable group such as 32P or any other detectable marker, such as other radioisotopes, a fluorescent compound, an enzyme or an enzyme co-factor. Probes for hybridization can be made by labeling synthetic oligonucleotides based on the known polypeptide-encoding nucleic acid sequences disclosed herein. Degenerate primers designed on the basis of conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequences encoding polypeptides or a fragment or variant thereof. Methods for the preparation of probes for hybridization and stringency conditions are generally known in the art and are disclosed in Sambrook and Russell, (2001), supra.

Nucleotide Constructs, Expression Cassettes and Vectors

The use of the term "nucleotide constructs" herein is not intended to limit the embodiments to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the polypeptide gene sequence of the disclosure to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments the DNA construct comprises a polynucleotide encoding an R gene polypeptide of the embodiments. In some embodiments the DNA construct comprises a polynucleotide encoding a fusion protein comprising an R gene polypeptide of the embodiments.

In some embodiments the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers are known in the art including for example, introns with gene expression enhancing properties in plants (US Patent Application Publication Number 2009/0144863, the ubiquitin intron (i.e., the maize ubiquitin intron 1 (see, for example, NCBI sequence S94464)), the omega enhancer or the omega prime enhancer (Gallie, et al., (1989) *Molecular Biology of RNA* ed. Cech (Liss, New York) 237-256 and Gallie, et al., (1987) *Gene* 60:217-25), the CaMV 35S enhancer (see, e.g., Benfey, et al., (1990) *EMBO J.* 9:1685-96) and the enhancers of U.S. Pat. No. 7,803,992 may also be used. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) (el/64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred usage. For example, although nucleic acid sequences of the embodiments may be expressed in both monocotyledonous and dicotyledonous plant species, sequences can be modified to account for the specific preferences and GC content preferences of monocotyledons or dicotyledons as these preferences have been shown to differ (Murray et al. (1989) *Nucleic Acids Res.* 17:477-498). Thus, the plant-preferred for a particular amino acid may be derived from known gene sequences from plants.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli* or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible or other promoters for expression in the host organism.

In some aspects, a DNA construct may encode a double stranded RNA targeting an effector protein transcript, producing a reduction in effector protein translation. In some embodiments, the reduction in effector protein produces a disease resistance phenotype in a plant or plant cell. A wide variety of eukaryotic organisms, including plants, animals, and fungi, have evolved several RNA-silencing pathways to protect their cells and genomes against invading nucleic acids, such as viruses or transposons, and to regulate gene expression during development or in response to external stimuli (for review, see Baulcombe (2005) *Trends Biochem. Sci.* 30:290-93; Meins et al. (2005) *Annu. Rev. Cell Dev. Biol.* 21:297-318). In plants, RNA-silencing pathways have been shown to control a variety of developmental processes including flowering time, leaf morphology, organ polarity, floral morphology, and root development (reviewed by Mallory and Vaucheret (2006) *Nat. Genet.* 38: S31-36). All RNA-silencing systems involve the processing of double-stranded RNA (dsRNA) into small RNAs of 21 to 25 nucleotides (nt) by an RNaseIII-like enzyme known as Dicer or Dicer-like in plants (Bernstein et al. (2001) *Nature* 409:363-66; Xie et al. (2004) *PLOS Biol.* 2 E104:0642-52; Xie et al. (2005) *Proc. Natl. Acad. Sci. USA* 102:12984-89; Dunoyer et al. (2005) *Nat. Genet.* 37:1356-60). These small RNAs are incorporated into silencing effector complexes containing an Argonaute protein (for review, see Meister and Tuschl (2004) *Nature* 431:343-49).

Plant Transformation

The methods of the embodiments involve introducing a polypeptide or polynucleotide into a plant. "Introducing" is as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide(s) or polypeptide(s) gains access to the interior of at least one cell of the plant. Methods for introducing polynucleotide(s) or polypeptide(s) into plants are known in the art including, but not limited to, stable transformation methods, transient transformation methods, and virus-mediated methods.

"Stable transformation" as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), Agrobacterium-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in *Plant Cell, Tissue, and Organ Culture: Fundamental Methods*, ed. Gamborg and Phillips, (Springer-Verlag, Berlin) and McCabe, et al., (1988) *Bio-technology* 6:923-926) and Lecl transformation (WO 00/28058). For potato transformation see, Tu, et al., (1998) *Plant Molecular Biology* 37:829-838 and Chong, et al., (2000) *Transgenic Research* 9:71-78. Additional transformation procedures can be found in Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio Technology* 6:923-926 (soybean); Finer and McMullen, (1991) *In Vitro Cell Dev. Biol.* 27P: 175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (*Longman*, New York), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via Agrobacterium tumefaciens).
Methods to Introduce Genome Editing Technologies into Plants In some embodiments, polynucleotide compositions can be introduced into the genome of a plant using genome editing technologies, or previously introduced polynucleotides in the genome of a plant may be edited using genome editing technologies. For example, the identified polynucleotides can be introduced into a desired location in the genome of a plant through the use of double-stranded break technologies such as TALENS, meganucleases, zinc finger nucleases, CRISPR-Cas, and the like. For example, the identified polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In some embodiments, where an R allele has been identified in a genome, genome editing technologies may be used to alter or modify the polynucleotide sequence. Site specific modifications that can be introduced into the desired R gene allele polynucleotide include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional disease resistant proteins in close proximity to the R gene polynucleotide compositions within the genome of a plant, in order to generate molecular stacks disease resistant proteins.

An "altered target site," "altered target sequence." "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

EXAMPLES

The following examples are offered to illustrate, but not to limit, the claimed subject matter. It is understood that the examples and embodiments described herein are for illustrative purposes only, and persons skilled in the art will recognize various reagents or parameters that can be altered without departing from the spirit of the disclosure or the scope of the appended claims.

Example 1. Identify Putative Pathogen Effectors

Puccinia polysora is the causal agent of Southern corn rust (SCR), a major disease in many maize-growing regions. A list of putative Puccinia polysora effectors were generated by computational analysis. RNA was isolated from germinating urodiospores and PacBio Iso-Seq was performed. Of all the cDNA sequences obtained, a total of 965 Puccinia polysora genes (PPG) were predicted by SignalP 4.0 (Petersen et al. 2011) to have signal peptides and code for secreted proteins. The secreted proteins with more than 1.8% cysteine were selected and PCR amplified from cDNA derived from infected leaf tissues. A total of 338 PPG cDNAs were successfully cloned into an expression vector, with the effector under the control of the strong constitutive 35S promoter.

Example 2. Identification of a Putative Effector Recognized by RppK

RppK, a SCR resistance gene, was previous identified and confirmed (See PCT/CN2018/090067). A protoplast-based system (Lu et al., 2016; Yoshida et al., 2009) was used to screen for effectors which can cause rapid protoplast death in the presence of RppK. Protoplasts isolated from transgenic RppK or null plants were co-transfected with plasmid DNA of the effector expression vector and a luciferase expression vector (driven by the 35S promoter). A significant reduction in luciferase activity indicates protoplast death, presumably caused by HR. Rp1-D21, an autoactive allele of the maize Rp1 disease resistance gene (Wang et al., 2015), was used as the positive control. An empty vector was used as the negative control. PPG1259 (SEQ ID NO: 4) was identified to cause strong HR in protoplasts from the RppK transgenic plants but did not in protoplasts from the null plants (See FIG. 1 and Table 1). Thus, the results show PPG1259 (SEQ ID NO: 4) as the putative pathogen effector or avirulence (Avr) gene which is recognized by RppK. It is a secretory protein without any known functional domain.

Figure 2:
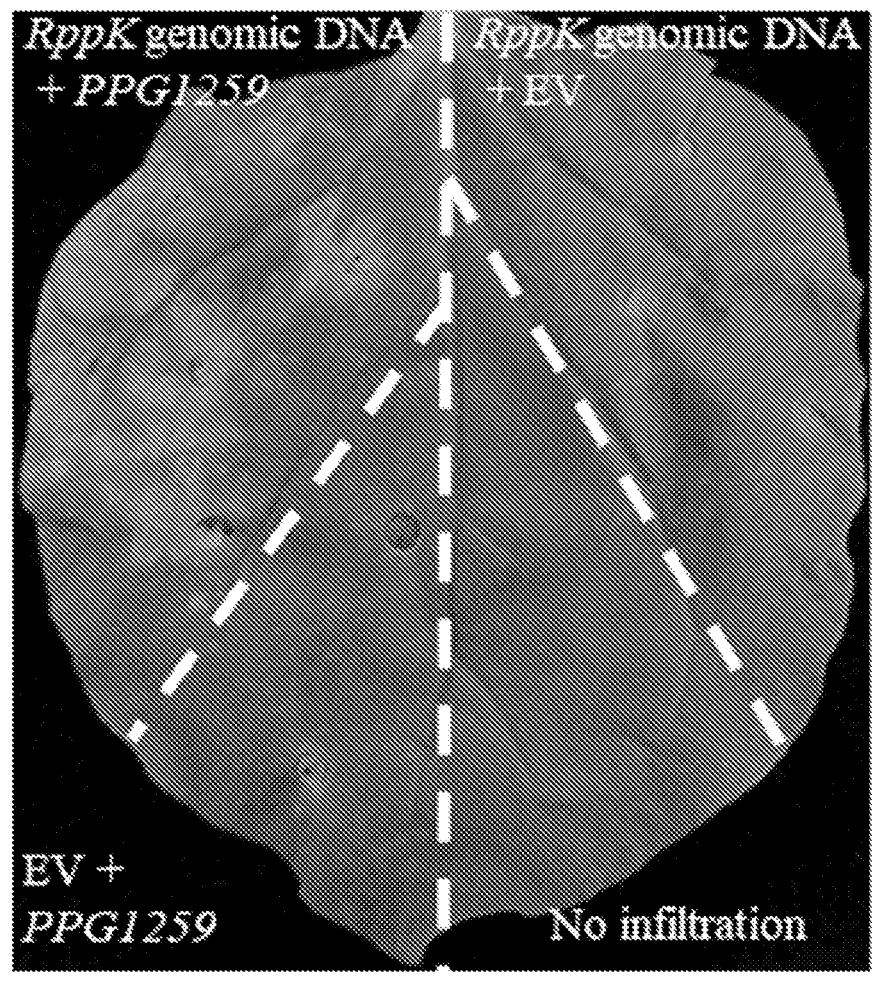
FIG. 2 shows coinfiltration of the constructs carrying Rppk genomic DNA and 35S:PPG1259 induces HR in Nicotiana benthamiana.
Figure 3:
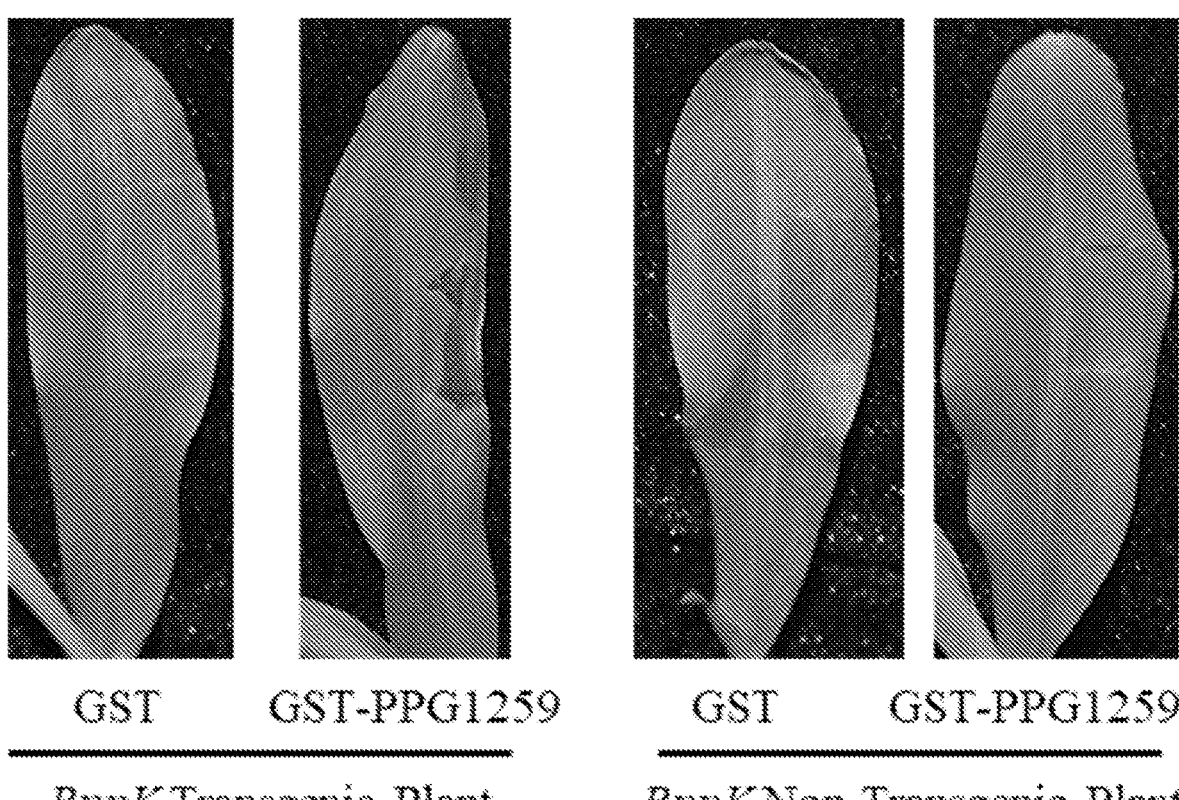
FIG. 3 shows infiltration of GST-PPG1259 protein causes cell death in leaves of Rppk transgenic plants.

Example 3. Identify and Confirm Effectors Recognized Disease Resistance Genes To confirm PPG1259 is the cognate effector recognized by RppK, the maize Rppk (genomic fragment) and PPG1259 genes were co-expressed in Nicotiana benthamiana by agroinfiltration. A clear HR was observed five days after infiltration. No HR was triggered by the transient expression of RppK or PPG1259 with an empty vector (EV) (FIG. 2). Furthermore, GST-tagged PPG1259 was expressed in E. coli and the purified recombinant protein was infiltrated into leaves of the Rppk transgenic and null plants. One day after the infiltration, clear cell death was observed on GST-PPG1259 infiltrated leaves of the RppK transgenic plants, while no HR was observed on GST-PPG1259 infiltrated leaves of null plants (FIG. 3). GST protein was used as a negative control (FIG. 3). Therefore, it is concluded that PPG1259 is the avirulence gene (AvrRppk) which is recognized by RppK to mediate effector triggered immunity (ETI).

TABLE 1

| | Relative luciferase activities | |
| --- | --- | --- |
| | Protoplasts from RppK transgenic plants | Protoplasts from null plants |
| PPG1259 | 0.252 ± 0.066 | 0.688 ± 0.164 |
| Rp1-D21 | 0.221 ± 0.067 | 0.057 ± 0.013 |
| Empty vector | 1 ± 0.026 | 1 ± 0.354 |

What is claimed:

1. A method of validating a causal disease resistance gene comprising:
   a. identifying at least one candidate gene in a disease resistance locus in a disease resistant maize plant;
   b. transfecting at least one allele of a plant pathogen effector gene and a luciferase gene into a maize protoplast, wherein the maize protoplast is derived from the disease resistant maize plant, and wherein the pathogen effector gene is from *Puccinia polysora* and encodes a polypeptide comprising a sequence having at least 995% sequence identity to SEQ ID NO: 4;
   c. measuring luciferase activity; and
   d. selecting a gene that produces a hypersensitive response in the presence of the plant pathogen effector.

2. The method of claim 1, further comprising:
   selecting a maize plant that expresses the selected gene of claim 1.

3. The method of claim 1, wherein breeding a plant for disease resistance comprising:
   providing the selected maize plant of claim 2;
   crossing said selected maize plant with a second maize plant; and
   selecting a progeny plant that produces a hypersensitive response in the presence of the plant pathogen effector.

4. A maize protoplast comprising a predicted pathogen effector gene from *Puccinia polysora*, and a luciferase gene, wherein the predicted pathogen effector gene is predicted from a computational analysis, and wherein the pathogen effector gene encodes a polypeptide comprising a sequence having at least 995% sequence identity to SEQ ID NO: 4; said maize protoplast further comprising a candidate maize disease resistance gene.

5. The maize protoplast of claim 4, wherein the predicted pathogen effector gene and the luciferase reporter gene are both expressed from a single expression vector.

6. A maize plant comprising a dsRNA targeting a pathogen effector protein from *P. polysora*, wherein the pathogen effector protein was identified or validated through a luciferase reporter protoplast assay, and wherein the pathogen effector comprises a sequence having at least 995% sequence identity to SEQ ID NO: 4.

7. A recombinant DNA construct comprising a polynucleotide operably linked to at least one regulatory sequence wherein said polynucleotide comprises a nucleic acid sequence encoding an amino acid sequence having at least 995% sequence identity to SEQ ID NO: 4.

8. The recombinant DNA construct of claim 7, wherein said at least one regulatory sequence is a promoter functional in a plant cell.

9. A plant cell comprising the recombinant DNA construct of claim 7.

10. The plant cell of claim 9, wherein the plant cell is derived from a disease resistant plant.

11. The plant cell of claim 9, wherein the plant cell is derived from a disease susceptible plant.

* * * * *